(12) United States Patent
McKenna et al.

(10) Patent No.: US 8,413,655 B2
(45) Date of Patent: Apr. 9, 2013

(54) ADSORBENTS AND INHALATION DEVICES

(75) Inventors: Douglas B. McKenna, Avondale, PA (US); Nicholas J. Dunlop, Wilmington, DE (US)

(73) Assignee: Micropore, Inc., Elkton, MD (US)

( * ) Notice: Subject to any disclaimer, the term of this patent is extended or adjusted under 35 U.S.C. 154(b) by 847 days.

(21) Appl. No.: 12/482,286

(22) Filed: Jun. 10, 2009

(65) Prior Publication Data
US 2009/0301493 A1 Dec. 10, 2009

Related U.S. Application Data

(60) Provisional application No. 61/060,386, filed on Jun. 10, 2008.

(51) Int. Cl.
*B01D 53/02* (2006.01)
*B01D 53/14* (2006.01)

(52) U.S. Cl. ......... 128/205.28; 128/205.12; 128/201.27; 96/139

(58) Field of Classification Search ............. 128/205.12, 128/204.13, 205.2, 205.27, 205.29, 206.16, 128/206.17, 206.19, 202.26, 201.27; 95/139, 95/486–487
See application file for complete search history.

(56) References Cited

U.S. PATENT DOCUMENTS

| 2,395,842 | A | | 3/1946 | Borgstrom |
| 2,629,652 | A | | 2/1953 | Schechter et al. |
| 2,812,769 | A | | 11/1957 | Schaefer et al. |
| 2,837,413 | A | * | 6/1958 | Hay ................................. 422/49 |
| 3,489,144 | A | | 1/1970 | Dibelius |
| 3,604,416 | A | | 9/1971 | Petrahai et al. |
| 3,607,040 | A | | 9/1971 | Hervert et al. |
| 3,860,818 | A | | 1/1975 | Stalder et al. |
| 3,909,206 | A | | 9/1975 | Katz |
| 4,153,661 | A | | 5/1979 | Ree et al. |
| 4,168,706 | A | | 9/1979 | Lovell |
| 4,342,278 | A | | 8/1982 | Horan |
| 4,342,811 | A | | 8/1982 | Lopatin et al. |
| 4,407,723 | A | | 10/1983 | MacGregor et al. |
| 4,409,978 | A | | 10/1983 | Bartos |
| 4,442,162 | A | | 4/1984 | Kuester |
| 4,508,700 | A | | 4/1985 | Hoshiko |
| 4,553,983 | A | | 11/1985 | Baker |
| 4,559,066 | A | | 12/1985 | Hunter et al. |

(Continued)

FOREIGN PATENT DOCUMENTS

EP 0171551 2/1986
WO WO 01/07114 2/2001

(Continued)

OTHER PUBLICATIONS

International Search Report and Written Opinion dated Aug. 12, 2009 for International Appln. No. PCT/US09/46939 (11 pgs.).

(Continued)

*Primary Examiner* — Stephen Crow
(74) *Attorney, Agent, or Firm* — Fish & Richardson P.C.

(57) ABSTRACT

An adsorbent is described. The adsorbent may include a membrane and an adsorbent material encapsulated within the membrane. An inhalation device is also described. The inhalation device may include a housing and a membrane within the housing. The membrane may encapsulate an adsorbent material. The membrane may be positioned such that airflow through the housing passes across but not through the membrane.

21 Claims, 15 Drawing Sheets

U.S. PATENT DOCUMENTS

| | | | |
|---|---|---|---|
| 4,631,872 A | 12/1986 | Daroga | |
| 4,642,996 A | 2/1987 | Harris et al. | |
| 4,665,050 A | 5/1987 | Degen et al. | |
| 4,707,953 A | 11/1987 | Anderson et al. | |
| 4,781,184 A | 11/1988 | Fife | |
| 4,985,296 A | 1/1991 | Mortimer, Jr. et al. | |
| 5,082,471 A | 1/1992 | Athayde et al. | |
| 5,165,399 A | 11/1992 | Hochberg | |
| 5,332,426 A | 7/1994 | Tang et al. | |
| 5,338,516 A | 8/1994 | Zhang et al. | |
| 5,449,014 A | 9/1995 | Yan-ho | |
| 5,665,148 A | 9/1997 | Mühlfeld et al. | |
| 5,742,516 A | 4/1998 | Olcerst | |
| 5,964,221 A * | 10/1999 | McKenna | 128/205.12 |
| 6,176,897 B1 | 1/2001 | Keefer | |
| 6,192,633 B1 | 2/2001 | Hilbert | |
| 6,247,471 B1 | 6/2001 | Bower et al. | |
| 6,349,508 B1 | 2/2002 | Ju et al. | |
| 6,385,919 B1 | 5/2002 | McCarthy | |
| 6,428,680 B1 | 8/2002 | Kreichauf | |
| 6,565,627 B1 | 5/2003 | Golden et al. | |
| 6,699,309 B1 | 3/2004 | Worthington et al. | |
| 6,797,043 B2 | 9/2004 | Nalette et al. | |
| 6,862,529 B2 | 3/2005 | Brown et al. | |
| 6,893,483 B2 | 5/2005 | Golden et al. | |
| 7,077,891 B2 | 7/2006 | Jaffe et al. | |
| 7,109,853 B1 | 9/2006 | Mattson et al. | |
| 7,196,023 B2 | 3/2007 | Langley et al. | |
| 7,282,464 B2 | 10/2007 | Kimmel | |
| 7,326,280 B2 | 2/2008 | Hrycak et al. | |
| 7,329,307 B2 * | 2/2008 | Hrycak et al. | 95/139 |
| 7,395,936 B2 | 7/2008 | Knight | |
| 7,407,533 B2 | 8/2008 | Steins | |
| 7,481,234 B1 | 1/2009 | Gustafson et al. | |
| 2001/0012494 A1 | 8/2001 | Kreichauf | |
| 2001/0053667 A1 | 12/2001 | Kreichauf | |
| 2002/0124490 A1 | 9/2002 | McCarthy | |
| 2002/0134246 A1 | 9/2002 | Babicki et al. | |
| 2002/0170436 A1 | 11/2002 | Keefer et al. | |
| 2003/0011948 A1 | 1/2003 | Saito et al. | |
| 2003/0205131 A1 | 11/2003 | Golden et al. | |
| 2005/0145224 A1 | 7/2005 | Zulauf et al. | |
| 2005/0160912 A1 | 7/2005 | Hrycak et al. | |
| 2005/0160913 A1 | 7/2005 | Hrycak et al. | |
| 2006/0048648 A1 | 3/2006 | Gibbs et al. | |
| 2006/0169142 A1 | 8/2006 | Rode et al. | |
| 2007/0200420 A1 | 8/2007 | McCormick | |
| 2007/0253872 A1 | 11/2007 | Keefer et al. | |
| 2008/0148936 A1 | 6/2008 | Baksh | |
| 2008/0282887 A1 | 11/2008 | Chance et al. | |
| 2009/0293720 A1 | 12/2009 | Liu | |
| 2011/0206572 A1 | 8/2011 | McKenna et al. | |
| 2012/0090470 A1 | 4/2012 | McKenna et al. | |

FOREIGN PATENT DOCUMENTS

| | | |
|---|---|---|
| WO | WO 2005/086613 | 9/2005 |
| WO | WO2006025853 | 3/2006 |
| WO | WO2007117266 | 10/2007 |
| WO | WO2009152264 | 12/2009 |
| WO | WO2011094296 | 8/2011 |
| WO | WO2012051524 | 4/2012 |

OTHER PUBLICATIONS

Battelle (Battelle News Release: Naval Sea Systems Command Issues Submarines Life-Saving Lithium Hydroxide Curtains Developed by Battelle) Apr. 6, 2004 http://www.battelle.org/news/04/4-06-04LithCurtain.stm, 2 pgs.

Daley, Tom "A New Approach to Non-Regenerative CO2 Removal", Submarine Air Monitoring and Air Purification Conference (SAMAP), San Diego, CA (Oct. 21, 2009), 25 pgs.

Davis, et al, "The Dependence of the CO2 Removal Efficiency of LiOH on Humidity and Mesh Size", presented by the American Society of Mechanical Engineers, at the Intersociety Conference on Environmental Systems, San Diego, California, Jul. 10-13, 1978, 7 pgs.

Davis, et al, "The Factors Influencing the Formation of Li2o3 from LiOH and CO2", presented by The American Society of Mechanical Engineers, at the Intersociety Environmental Systems Conference, San Diego, California, Jul. 14-17, 1980, 6 pgs.

General Specification NASA-JSC, Requirements for Lithium Hydroxide Used for CO2 Removal in Closed Environments, National Aeronautics and Space Administration, Houston, Texas, Oct. 1994, 30 pgs.

"Lithium Hydroxide, Anhydrous", pamphlet CAS No. 1310-65-2, FMC Corporation, copyright 2001, 2 pgs.

Military Specification for Lithium Hydroxide (LiOH), Technical, MIL-L-20213E, Naval Sea Systems Command, Jun. 18, 1980, 12 pgs.

The American Heritage Dictionary of the English Language: Fourth Edition 2000, 2 pgs.

Wang, "Residence Time and Carbon Dioxide Scrubbing Efficiency in Life Support Systems", Aviation Space and Environmental Medicine, Feb. 1981, pp. 104-108.

Webster's Third New International Dictionary, unabridged, 1993, downloaded from the Internet on Nov. 19, 2009, http://lionreference.chadwyck.com/searchFulltext.do?id=31052187&idType=offset&divLevel=2... , 1 pg.

Examiner's First Report dated Oct. 10, 2007 for Australian Appln. No. 2005280633, 2 pgs.

International Preliminary Report on Patentability and Written Opinion dated Jul. 31, 2006 for International Appln. No. PCT/US2005/003480, 8 pgs.

International Preliminary Report on Patentability and Written Opinion dated Jul. 8, 2008 for International Appln. No. PCT/US2006/031847, 6 pgs.

International Preliminary Report on Patentability and Written Opinion dated Dec. 13, 2010 for International Appln. No. PCT/US2009/046939, 9 pgs.

International Search Report dated Feb. 1, 2006 for International Appln. No. PCT/US2005/003480, 3 pgs.

International Search Report dated Apr. 30, 2008 for International Appln. No. PCT/US2006/031847, 3 pgs.

International Search Report and Written Opinion dated Mar. 29, 2011 for International Appln. No. PCT/US11/22556, 7 pgs.

International Search Report and Written Opinion dated Feb. 16, 2012 for International Appln. No. PCT/US2011/056345, 12 pgs.

* cited by examiner

L CO₂ Scrubbed Per g / average pressure drop

ADSORBENTS AND INHALATION DEVICES

This application claims priority to U.S. Provisional Patent Application No. 61/060,386, filed Jun. 10, 2008; the content of which is incorporated by reference in its entirety.

FIELD OF THE INVENTION

The present invention relates to adsorbents and, more specifically, to use of adsorbents in inhalation devices to reduce inhalation of target materials by a user.

BACKGROUND OF THE INVENTION

Research has shown that some patients who suffer from anxiety attacks and/or panic disorders are extremely sensitive to small variations in carbon dioxide ($CO_2$) levels. The known elevation of $CO_2$ in closed-in, agoraphobic or claustrophobic environments is one causative factor of panic attacks in patients diagnosed with panic disorder. Panic attacks resemble suffocation. Panic attack patients have lower blood $CO_2$ and are more sensitive to increases of $CO_2$.

Anxiety has been defined as a feeling of fear, dread or apprehension that arises without clear or appropriate justification. Anxiety includes a number of symptoms that are physical, psychological and behavioral in nature. Anxiety during a panic attack may manifest itself in a number of physical signs that are typically produced from over-activity of the sympathetic nervous system or even from tension in the skeletal muscles. These physical manifestations include palpitations, dry mouth, and dilation of the pupils, sweating, throat tightening, trembling, dizziness and even nausea. Psychological manifestations include irritability, restlessness and loss of concentration. Behavioral manifestations primarily include avoidance behavior, such as running away from a feared object or situation.

The effects of elevated levels of inspired carbon dioxide on the human brain have been studied. Specifically, carbon dioxide's local tissue vasodilatation effect is the major factor affecting cerebral blood flow. In healthy people, low concentrations of inspired $CO_2$ have been found to produce central nervous system stimulation. For example, the administration of 5% $CO_2$ has been shown to produce mental confusion, brain vasodilatation, elevated blood pressure and pulse, increased myocardial contractility and constriction of skeletal muscles. Concentrations of 10% or higher have a central nervous system depressant effect in healthy people and may lead to loss of consciousness within as little as 10 minutes. At concentrations of 30%, carbon dioxide becomes an anesthetic.

As shown in FIG. 1, analysis of air samples taken from environments commonly avoided by individuals with a panic disorder have shown increased levels of $CO_2$ up to 315% higher than normal outside air. The level of $CO_2$ in outside air is typically 0.03% or 300 ppm (parts per million). As shown in FIG. 1, the highest levels of $CO_2$ recorded, i.e., just below 0.1% or 1,000 ppm, were collected in a medical center elevator with 10 passengers, an automobile with 3 persons inside and no open windows, and a small jet aircraft fully loaded with passengers and the exit door closed. Typical elevated $CO_2$ levels of 0.06% or 600 ppm to 0.075% or 750 ppm, twice that of outside air, were collected in a range of environments such as restaurants, conference rooms, church services and classrooms.

At the onset of an anxiety attack a patient may use an inhalation device to lower the amount of $CO_2$ sensed by the individual. Patients may use a portable device containing $CO_2$ adsorbent through which to inhale at the onset of experiencing symptoms of their disorder. The adsorbent may reduce inspired $CO_2$ levels from the elevated level experienced in the current environment. Reducing inspired $CO_2$ levels may, in whole or in part, alleviate a panic attack and, thereby, accommodate the patients' disability. Of paramount importance is that the device offers the lowest possible breathing resistance and minimizes the risk of inhaling adsorbent particulates, while offering excellent $CO_2$ adsorption.

Traditional $CO_2$ adsorbents are typically manufactured by mixing hydrated lime with water and optionally a small amount of sodium or potassium hydroxide to form a paste, which is then extruded or molded in particles in granular or pellet form. These soda lime adsorbents are typically used in rebreather devices such as anesthesia machines and underwater breathing systems, where expired breath passes through a canister filled with adsorbent material where it is cleansed of $CO_2$, before being inhaled by a user. Soda lime adsorbents have limited value for individual inhalation devices because they have a limited ability to adsorb $CO_2$ when the devices for adsorption are small in size.

Adsorbent granules or pellets are loaded into a rebreather device in loose particulate form by pouring into an adsorber or supplied in pre-packed disposable containers for insertion into the adsorber. Adsorbent granules or pellets are generally sized between about 0.04 to 0.25 inches (1.0 to 6.5 mm) in diameter.

To achieve minimal breathing resistance, larger adsorbent particles are employed to allow gas flow around the granules, which offers a relatively low-pressure drop. Smaller granules allow more surface area per unit weight for greater $CO_2$ adsorption, however, an increase in breathing resistance in experienced.

Granules by their very nature are different shapes and sizes leading to variable performance, non-uniform depletion, channeling, strike through and wastage of un-exhausted granules. Additionally, granules have a tendency to grind together when packed and when being transported, which produces particulates or dust. Space consuming filters can be introduced to minimize inhalation of particulates; however, this introduces an unwanted resistance to breathing.

The ongoing trade-off between $CO_2$ removal rate, low-pressure drop, high $CO_2$ absorption capacity and size of adsorbent bed is a major limitation of granules. Granule manufacturers have tried to address these limitations by introducing alternative shapes and different formulations; however, the inherent flaws still exists.

Needs exist for improved adsorbents and inhalation devices that use improved adsorbents.

SUMMARY OF THE INVENTION

Embodiments of the present invention solve many of the problems and/or overcome many of the drawbacks and disadvantages of the prior art by providing methods and systems for adsorbents and inhalation devices.

Embodiments of the present invention may include adsorbents. The adsorbents may include a membrane, for example a sheet, and an adsorbent material encapsulated within the membrane. Embodiments of the present invention may also include an inhalation device. The inhalation device may include a housing and a membrane within the housing. The membrane may encapsulate an adsorbent material. The membrane may be positioned such that airflow through the housing passes across but not through the membrane.

A purpose of certain embodiments of the present invention is to provide an adsorbent system that offers little or no risk of inhalation of the adsorbent. It is also a purpose of certain embodiments of the present invention to provide an adsorbent that offers increased removal rates without the penalty of increased pressure drop. It is also a purpose of certain embodiments of the present invention to an adsorbent that can be operated in any orientation without affecting the performance of the system. It is also a purpose of certain embodiments of the present invention to maximize the duration that the system adsorbs a target material. It is also a purpose of certain embodiments of the present invention to allow both inhaled air and exhaled breath to be passed through the system. It is also a purpose of certain embodiments of the invention to allow the system to be robust enough for portable use. These and other purposes of the present invention will become evident from review of the following specification.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE PREFERRED EMBODIMENTS

Figure 1:
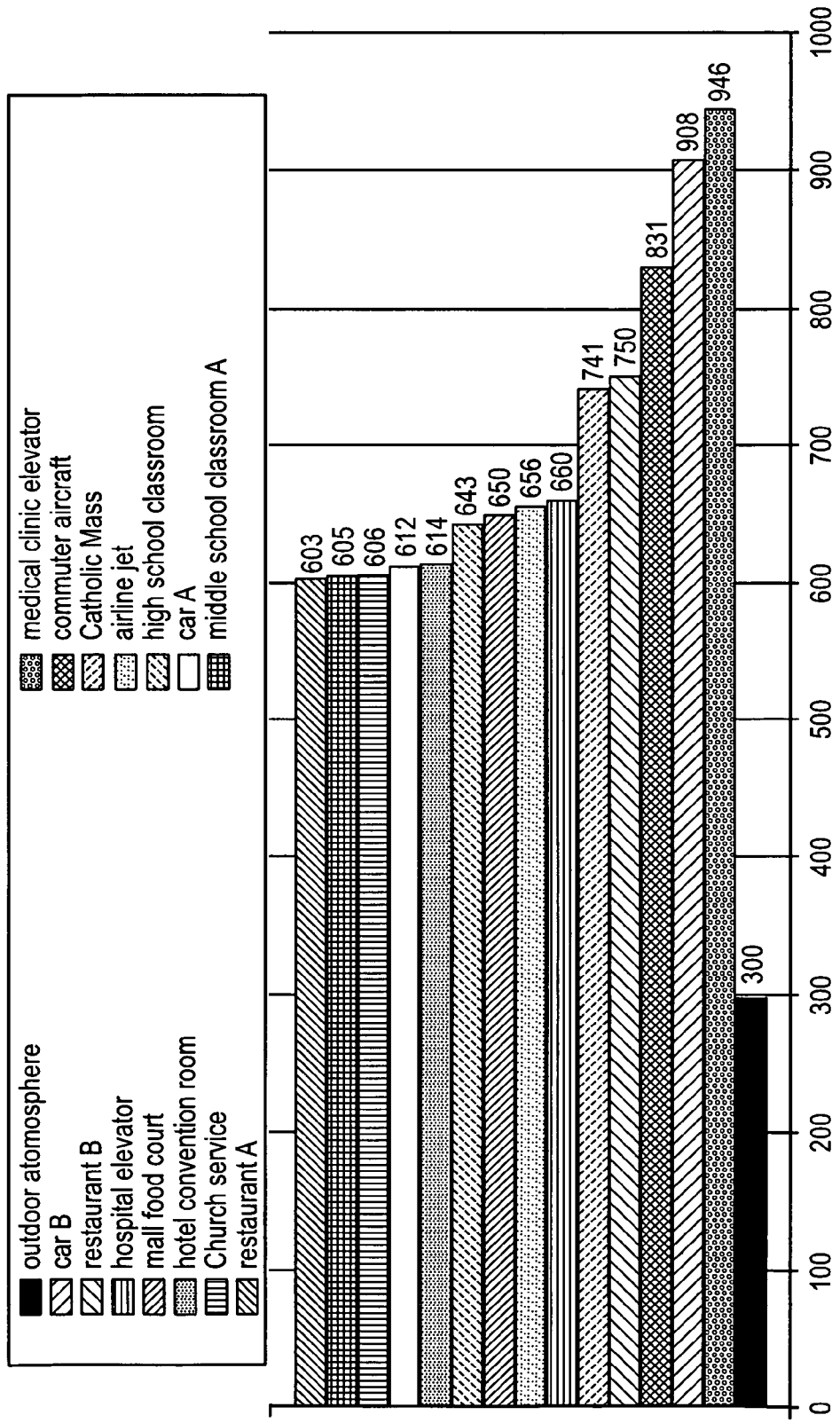
FIG. 1 is a graph of an analysis of air samples taken from environments commonly avoided by a person with panic disorder.

The present invention may provide an efficient means to reduce the levels of a target material inhaled, while offering uniform and consistent depletion of adsorbent material, containment of the adsorbent material to minimize any dusting risk, and a minimum pressure drop for the gases passing to the patient. Additionally, the present invention may be portable, easy and quick to install. While reduction of $CO_2$ is used as an exemplary target material, other target materials may be reduced by the present invention, such as contaminants within chemical, biological, radiological and nuclear (CBRN) applications.

The present invention may also be used as a means to reduce $CO_2$ within manned or unmanned devices, on either or both the inhalation or exhalation side, for levels as high as about 20% $CO_2$ or as low as about 300 ppm. One example being the invention may be part of a respiratory breathing circuit, for example an anesthesia or ventilator machine, or underwater breathing apparatus. The invention may be installed into a machine or patient breathing tube, such as used on anesthesia/ventilator machines, to adsorb $CO_2$ for single patient use. Devices such as anesthesia/ventilator machines or underwater breathing systems typically contain a $CO_2$ absorption mechanism, for example canisters or tube sections with $CO_2$ absorption material, within the machine or breathing tube.

Embodiments of the present invention may reduce $CO_2$ levels of inspired air. As the mechanism for removing $CO_2$ from a gas or inhaled air is dependent on the particular material chosen, the use of the word "adsorption" in this specification is meant to include adsorption, absorption, chemisorption, and so forth. The present invention may typically operate at $CO_2$ levels of lower than approximately 5,000 ppm, and more specifically lower than approximately 1,000 ppm or less. This is in contrast to existing rebreather devices that may typically operate at $CO_2$ levels of approximately 30,000 ppm to 40,000 ppm levels.

Embodiments of the present invention may be useful for patients suffering from anxiety attacks and/or panic disorders where low levels of $CO_2$ need to be filtered.

In certain embodiments, the adsorbent membrane of the present invention may be in a flat sheet form. Other forms include, but are not limited to, extruded forms where gas flow channels are molded directly into the adsorbent. Embodiments of such forms are described in U.S. Pat. Nos. 5,964,221, 7,326,280 and 7,329,307, all incorporated by reference in their entireties. The adsorbent membrane may be produced in various forms, such as smooth or with grooves. The grooves impart protrusions, such as a permanent rib structure, into the membrane, thereby forming the basis for flow channels. The properties of the adsorbent sheet are such that no other supporting or containment fabric or material is needed to maintain structural integrity or rigidity. Membranes, such as sheets, containing the adsorbent material can be formed in several ways to achieve optimum performance for the specific application. In one form, the $CO_2$ removal system of the present invention includes chemical adsorbent that is encapsulated in a waterproof, gas permeable membrane that has a high degree of particulate filtration efficiency. This construction comprehensively addresses many of the inherent problems that exist with granules. Adsorbent membranes are deployed in both rolled and flat form based of the specific application. For example, a membrane may be hung, or one or more sheets may be stacked. A ribbed membrane rolled or stacked onto itself may create channels for gas flow around the membrane. When used as a cartridge or in a canister or other type of housing for the adsorbent membrane, a rolled sheet is preferred. The rolled sheet may be twisted, for example spiraled. A rolled sheet embodied in the invention is described in U.S. Pat. No. 5,964,221, incorporated by reference. The chemical adsorbent, as described in U.S. Pat. Nos. 7,326,280 and 7,329,307 and incorporated by reference in their entireties, may be composed of for example, calcium hydroxide (CaOH) or lithium hydroxide (LiOH) adsorbent, which has an initial water content above an anhydrous level. The pre-hydrated carbon dioxide adsorbent or compound provides for higher rates of removal of $CO_2$ over longer periods of time and produces lower temperatures. The pre-hydrated LiOH carbon dioxide adsorbent compound reacts opposite to previous studies that show pre-hydrated LiOH granules performing the same or worse than anhydrous LiOH granules. One reason for the differing and unexpected results is the LiOH adsorbent density. In one embodiment, the LiOH adsorbent density is at or below 1.0 g/cm$^3$. A method for removing $CO_2$ may be performed by including pre-hydrated LiOH adsorbent in a membrane, such as a sheet, having airflow with carbon dioxide. Molecular sieves, activated carbon or other adsorbent materials may be used for removal of carbon dioxide or other contaminants. Molecular sieves, activated carbon or other adsorbent materials may be used particularly for CBRN applications.

Membranes may vary in at least thickness and separator height. As described in U.S. Pat. No. 5,964,221, which is incorporated by reference, the manufacturing process may allow for an adjustable sheet thickness for different applications. Ranges of sheet thickness for particular applications may be approximately about 0.001 inches to about 0.10 inches. In some applications, however, a preferred sheet thickness may be approximately 0.010 to about 0.050 inches. A more preferred sheet thickness may be approximately 0.010 to about 0.030 inches. In other embodiments, sheet thickness may be as low as about 0.001 inches, preferably about 0.001 to 0.010 inches. Sheets with thicknesses as low as about 0.001 inches may be applied to a backing material for support. Additionally, a backing material may be sandwiched between multiple layers of sheets with sheet thickness as low as about 0.001 inches. Additionally, the sheets may be manufactured with or without integral separating means. For example, if a device is manufactured without an integral separating means, the result may be a flat sheet. Ranges for integral separating means height for particular applications may be approximately 0.005 inches to 0.032 inches of height. In some applications, however, a preferred integral separating means height may be approximately 0.005 inches to about 0.025 inches. Sheet thickness and integral separator means height can be independently controlled during the manufacturing process. Independent control may allow for optimum performance of $CO_2$ removal rate, pressure drop and $CO_2$ adsorption, within the physical constraints of an inhalation device.

The sheet construction may overcome inherent limitations associated with granular adsorbent products. First, by encapsulating the $CO_2$ adsorbent material in a membrane that has a high degree of particulate efficiency, there is little or no risk of any particles being inhaled by a user. Second, because the membrane is gas permeable, $CO_2$ may readily pass through the membrane and be adsorbed in the membrane. Third, because the inspired gases flow past these membranes and not through them, the pressure drop is very low, resulting in a system that is easy to inhale through. Fourth, as the cartridge consists of a single rolled sheet, the process of refilling the device is easier, safer and more convenient. Fifth, the cartridge can be orientated to any position and withstand vibrations and shock without affecting its performance, thereby allowing the device to be portable.

Figure 14A:
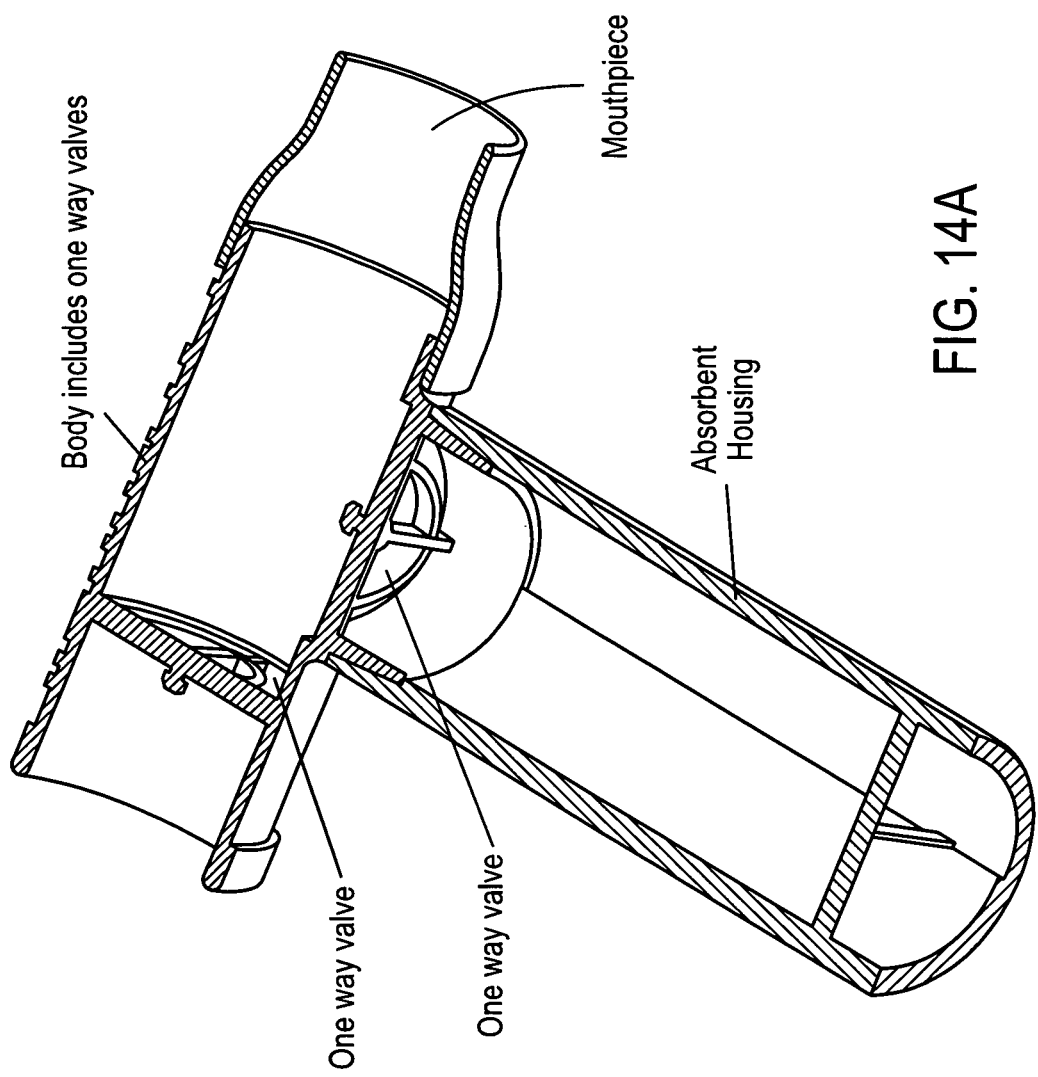
FIG. 14 shows an exemplary inhalation device for treating patients.

Embodiments of the present invention may also use adsorbent in a cartridge form. For a cartridge form, the sheet may be rolled into a small cartridge form for use, for example, within a hand-held device. Such a hand-held device is particularly useful for an anxiety attack or other panic disorder. This cartridge form affords the patient the added security of availability wherever or whenever they experience symptoms of, for example, an anxiety attack, with no degradation of performance of the adsorbent by shock and vibration in the portable environment. For example, there may be no change in breathing resistance, $CO_2$ capacity and rate of absorption. A sheet may be rolled onto a central solid or hollow, flexible core, or onto itself, based on the actual integration and design of the anxiety device. Winding onto a flexible core, such as a foam core, may increase performance characteristics with minimal or no increase in pressure drop. A cartridge may be any shape, for example cylindrical, cubed, octagonal, etc. FIGS. 14a & b show one form of a hand-held inhalation device that may be of any size amenable for carrying or storing for personal use.

To meet the requirement of an inhalation device, the cartridge must be of a size to allow the hand-held device and specifically the adsorbent housing to be held comfortably and easily in one hand. The cartridge diameter range may be approximately 1.125"±0.125" giving a cross sectional area range of approximately 0.75 sq. inches to approximately 1.3 sq. inches, with a height range of approximately 2.875"±0.125". Height is used as an exemplary dimension to represent the distance/direction that the gas travels as it passes through the adsorbent, and volume may also represent size dimension. A preferred maximum range of cross sectional area to height ratio can be about 95 to 1. A preferred minimum range of cross sectional area to height ratio can be about 0.05 to 1. While the data described herein is based on the cartridge size of the specified cross sectional area and length it is understood by those knowledgeable in the art that larger or smaller diameters or lengths of filters utilizing adsorbent materials as described herein could be used to vary the absorptive capacity versus pressure drop ratio.

It is apparent from the data contained herein that granular based anxiety filters have a problem with pressure drop and absorption capacity. As such granular filters with greater than a 0.5, 0.75 and 1 or even higher ratio of diameter versus length are desirable. Filters of the present invention can be made with minimum ratios of diameter versus length of about 0.05 to about 1, while still achieving the lowest pressure drops. Additionally, filters of the present invention can be made with maximum ratios of about 1 to about 11 that may have the effect of making the resistance to airflow almost immeasurable.

The device may be a personal carbon dioxide adsorption device capable of being discreetly carried in the pocket of a patient. As many patients may be uncomfortable revealing their condition in public, a small size allows the patient to carry the device without alerting others to their condition. To meet the requirement of the device the cartridge may be of a weight to allow the device and specifically the adsorbent housing to be held comfortably and easily in one hand during use. The cartridge weight, from the tests undertaken, may range from approximately 36 g to approximately 43 g. The variation may be dependant on the actual configuration of the sheet thickness and separator height of the specific sample. While the data described herein is based on the weight range to fit into the specified cross sectional area and length of cartridge, it is understood by those knowledgeable in the art that larger or smaller diameters or lengths of filters utilizing adsorbent materials as described herein could be used to vary the weight and the subsequent absorptive capacity versus pressure drop ratio.

It is apparent from the data contained herein that granular based anxiety filters can have a problem with pressure drop and absorptive capacity. As such granular filters require larger diameters to decrease pressure drop, and/or greater length to achieve the absorptive capacity. In both cases the resultant weight increase of adsorbent should not be such that the device cannot be held comfortably and easily.

Figure 2:
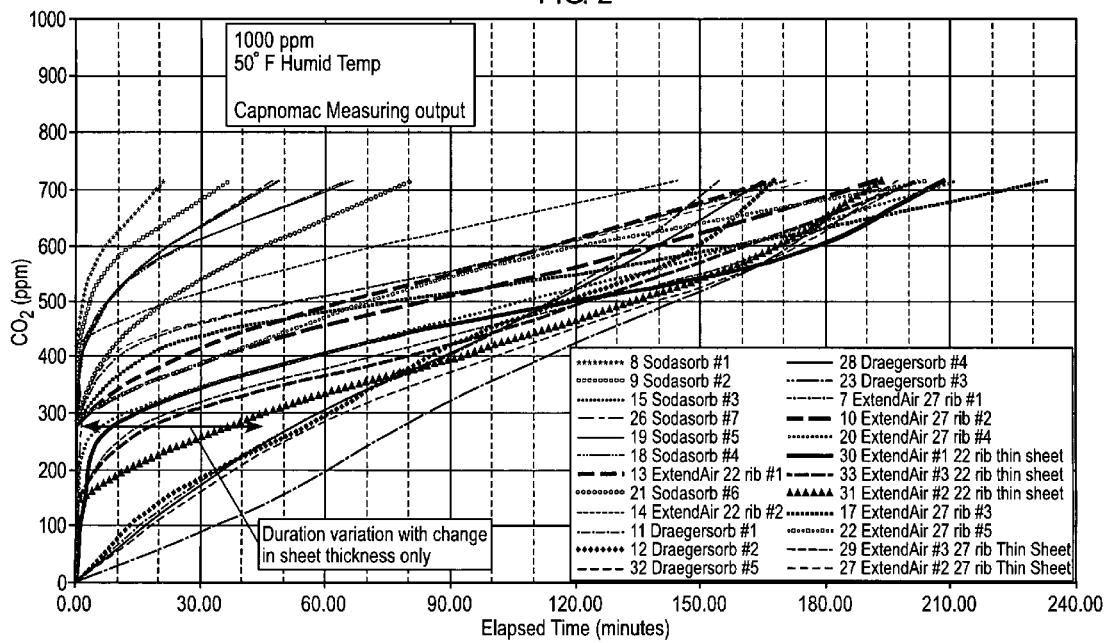
FIG. 2 is a graph of filter outlet $CO_2$ concentration (ppm) as a function of time (minutes).

FIG. 2 illustrates levels of $CO_2$ (ppm) as a function of time. The present invention may efficiently lower elevated levels of inhaled $CO_2$ (1000 ppm), by a minimum of approximately 30% for a period up to approximately 180 minutes or more, while maintaining an average breathing resistance of less than approximately 0.4 inches of water and a maximum of less than approximately 1.332 inches of water.

The present invention may efficiently lower elevated levels of inhaled $CO_2$ (1000 ppm), by a minimum of approximately 50% for a period up to approximately 120 minutes or more, while maintaining an average breathing resistance of less than approximately 0.4 inches of water and a maximum of less than approximately 1.332 inches of water.

The present invention may efficiently lower elevated levels of inhaled $CO_2$ (1000 ppm), by a minimum of approximately 70% for a period up to approximately 45 minutes or more, while maintaining an average breathing resistance of less than approximately 0.32 inches of water and a maximum of less than approximately 1.080 inches of water.

Figure 3:
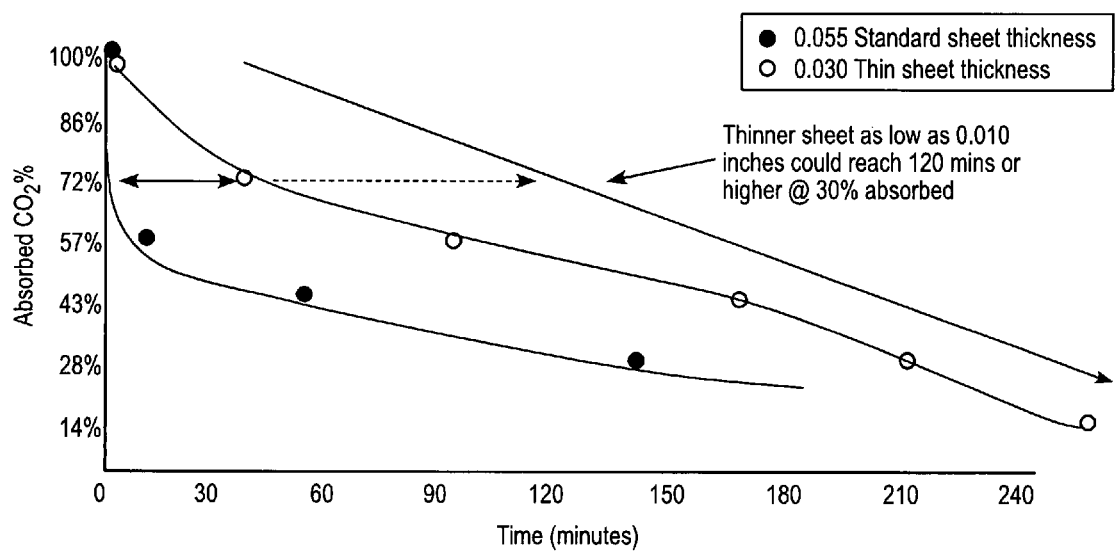
FIG. 3 is a graph of $CO_2$ adsorption rate versus time for varying sheet thicknesses.

FIG. 3 shows $CO_2$ (ppm) adsorption rate versus time for various sheet thickness. As shown in FIG. 3, by further reducing sheet thickness an initial absorption rate of 70% may be expected to have a longer duration. Sheet thickness may have a marked impact on adsorption rates. Durations may reach as high as approximately 120 minutes or even approximately 150 minutes with thinner sheets.

Figure 4:
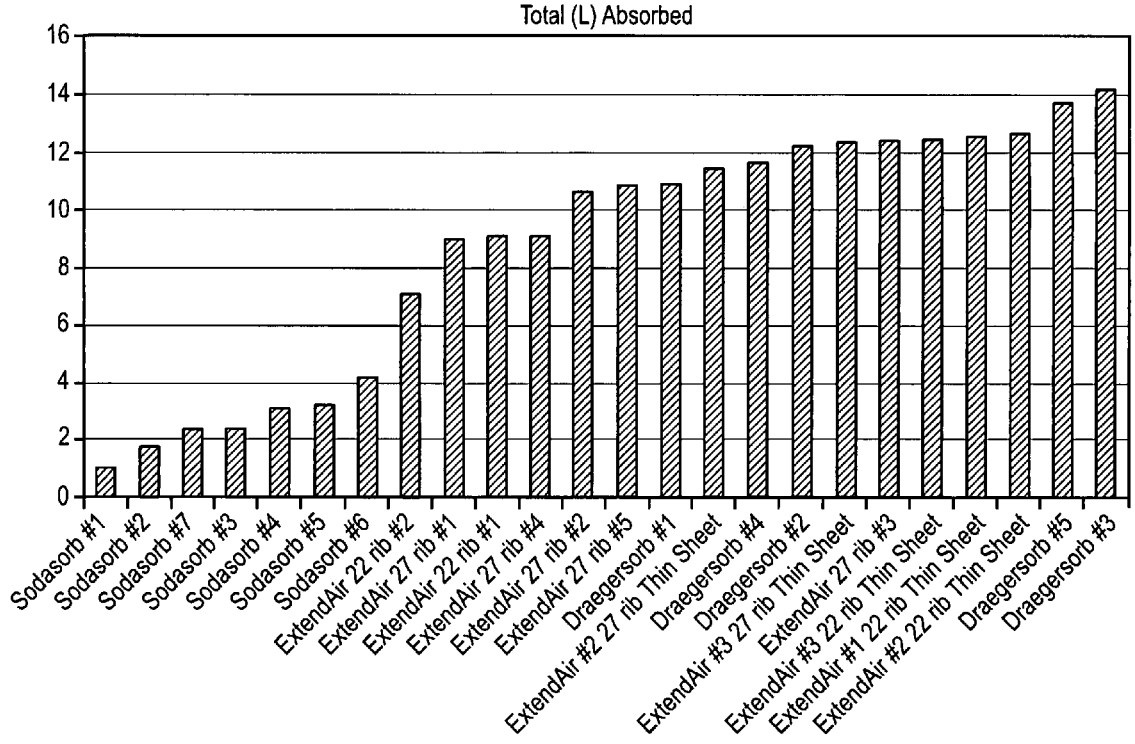
FIG. 4 is a graph of total $CO_2$ adsorbed for various adsorbents.

FIG. 4 illustrates amounts of $CO_2$ adsorbed for various adsorbents. For example, a minimum of 7.0L of $CO_2$ may be adsorbed while lowering inhaled $CO_2$ (1,000 ppm) by a minimum of 30%, while maintaining an average breathing resistance of less than 0.4 inches of water. A minimum of 10.8L of $CO_2$ may be adsorbed while lowering inhaled $CO_2$ (1,000 ppm) by a minimum of 30%, while maintaining an average breathing resistance of less than 0.38 inches of water. A minimum of 12.6L of $CO_2$ may be adsorbed while lowering inhaled $CO_2$ (1,000 ppm) by a minimum of 30%, while maintaining an average breathing resistance of less than 0.32 inches of water.

Figure 5:
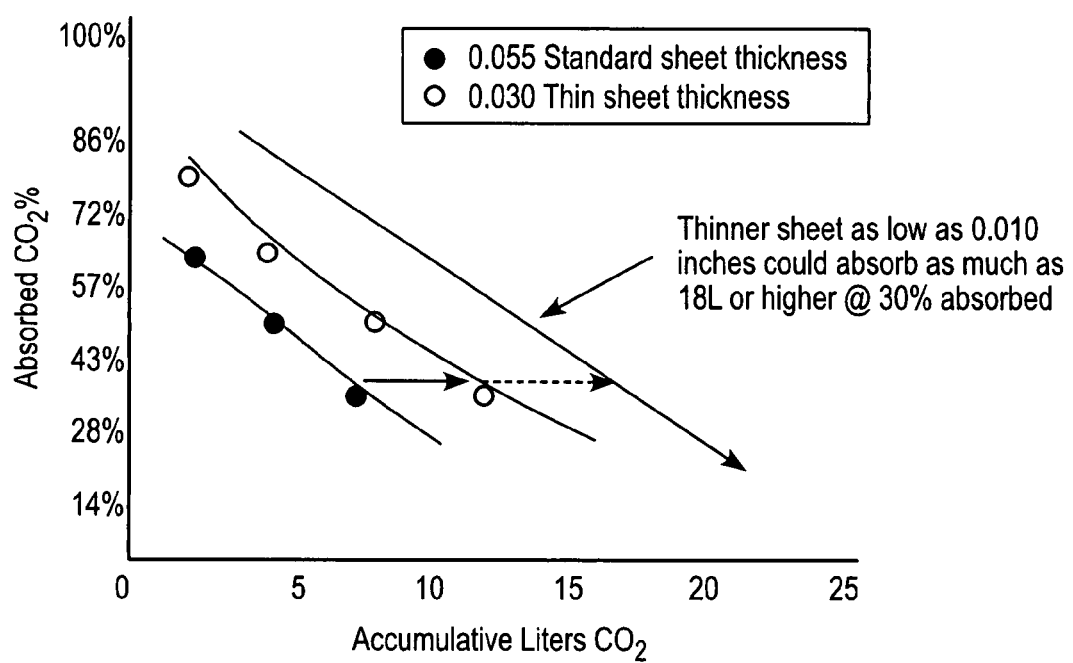
FIG. 5 is a graph of $CO_2$ adsorption rate versus total adsorbed for varying sheet thicknesses.

FIG. 5 illustrates $CO_2$ adsorption rate versus total adsorbed for various sheet thickness. As shown in FIG. 5, by further reducing the sheet thickness the $CO_2$ adsorbed may increase from 12.5L to as much as 18L or higher, while lowering inhaled $CO_2$ (1000 ppm) by a minimum of 30%.

Figure 6:
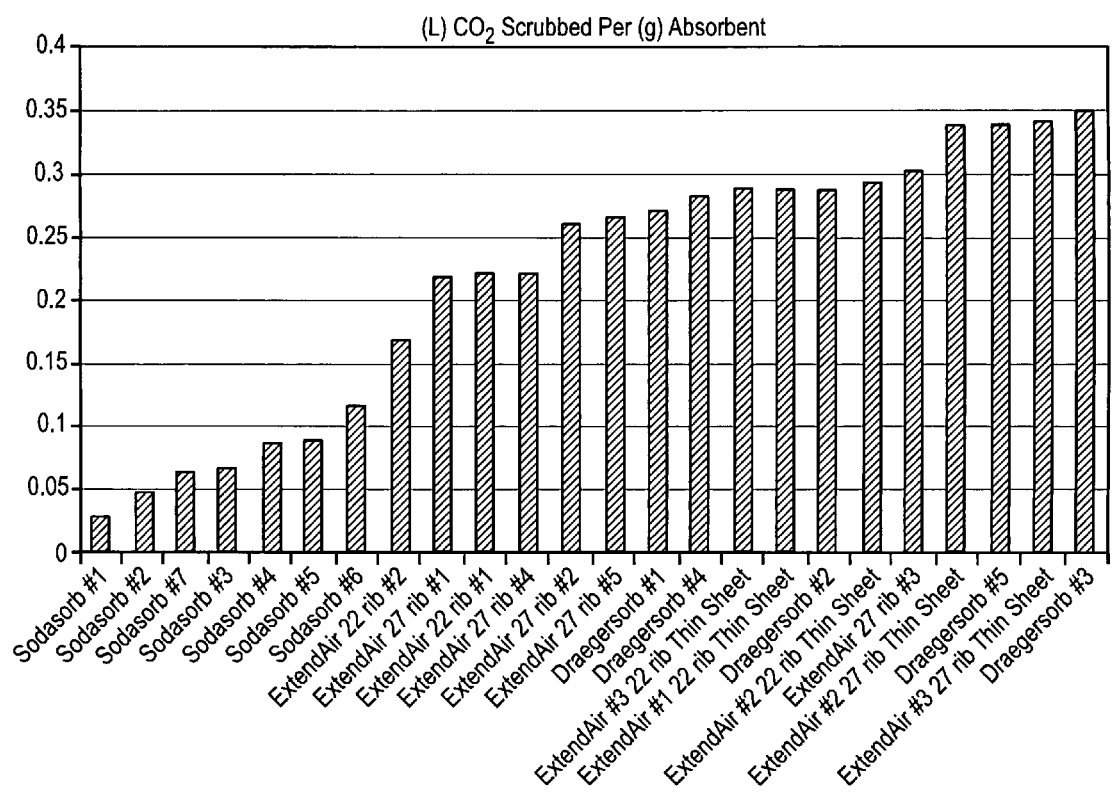
FIG. 6 is a graph of $CO_2$ litres adsorbed per gram of adsorbent.

FIG. 6 illustrates an amount of $CO_2$ adsorbed by weight. A minimum $CO_2$ adsorption of 0.171 L/g to 0.341 L/g may be attainable, while maintaining an average breathing resistance of less than 0.4 inches of water and while lowering inhaled $CO_2$ (1000 ppm) by a minimum of 30%.

Figure 7:
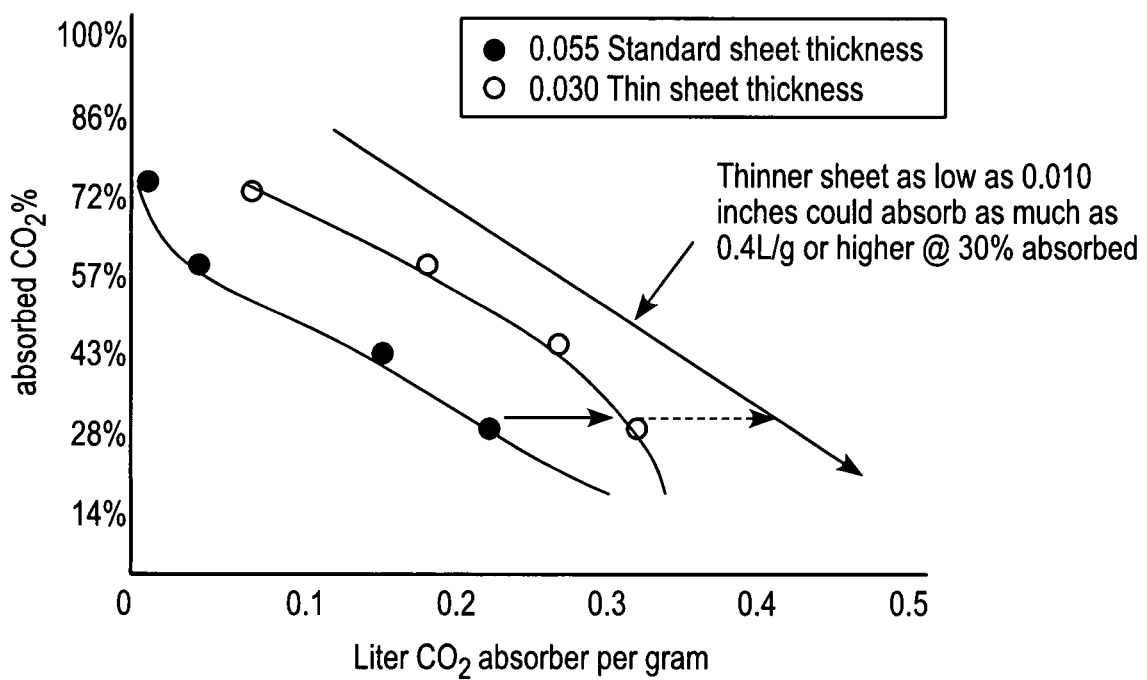
FIG. 7 is a graph of rate of $CO_2$ adsorbed per gram for varying sheet thicknesses.

FIG. 7 illustrates adsorbed $CO_2$ as a function of litres of adsorbent per gram. As shown in FIG. 7, by further reducing the sheet thickness the liters $CO_2$ scrubbed per gram adsorbent may increase to between 0.35 L/g-0.4 L/g or higher, while lowering inhaled $CO_2$ (1000 ppm) by a minimum of 30%.

Figure 8:
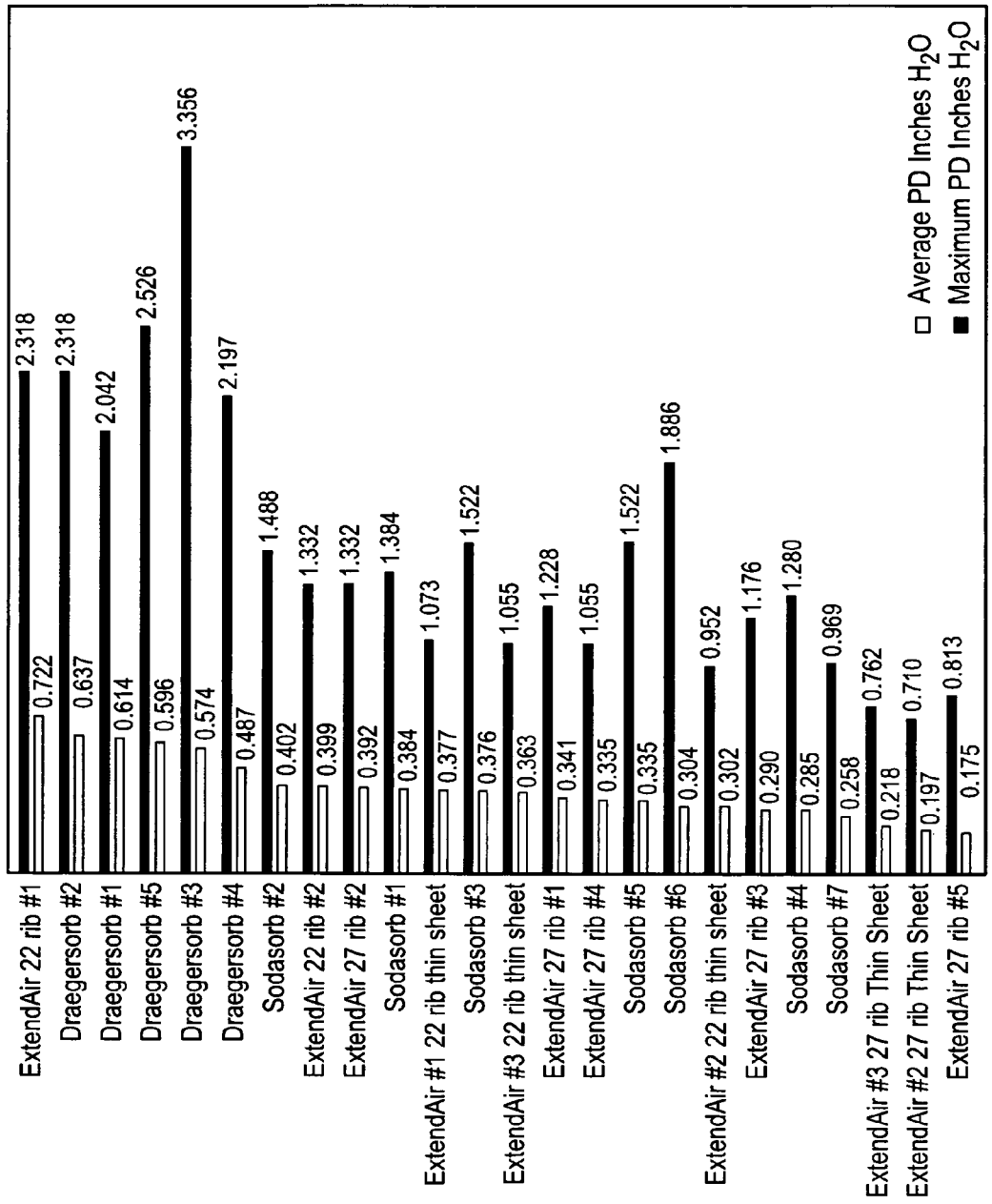
FIG. 8 is a graph of average and maximum pressure drop for various adsorbents while lowering inhaled $CO_2$ (1000 ppm) by a minimum of 30%.

FIG. 8 illustrates an amount of $CO_2$ adsorbed over average pressure drop. An average pressure drop range of 0.722 to 0.175 inches of water may be present for the invention, while lowering inhaled $CO_2$ (1000 ppm) by a minimum of 30%. Typically the expected range would be between 0.399 to 0.175 inches of water; however the actual pressure drop can be adjusted to suit the requirements of the application.

Figure 9:
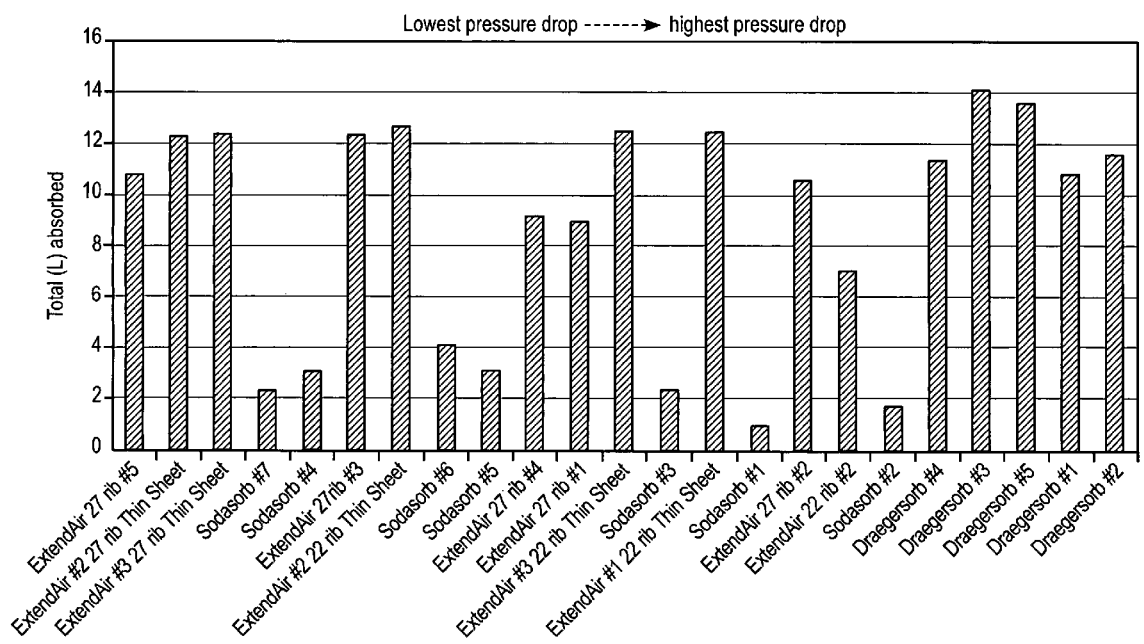
FIG. 9 is a graph of $CO_2$ adsorbed versus pressure drop or breathing resistance (inches of water), while lowering inhaled $CO_2$ (1000 ppm) by a minimum of 30%. (Pressure drop increases from Left to Right)

For this application, it may be desirable to have excellent absorption capacity while maintaining acceptable breathing resistance. FIG. 9 shows samples tested, the horizontal axis shows increased pressure drop from left to right, while lowering inhaled $CO_2$ (1000 ppm) by a minimum of 30%.

Figure 10:
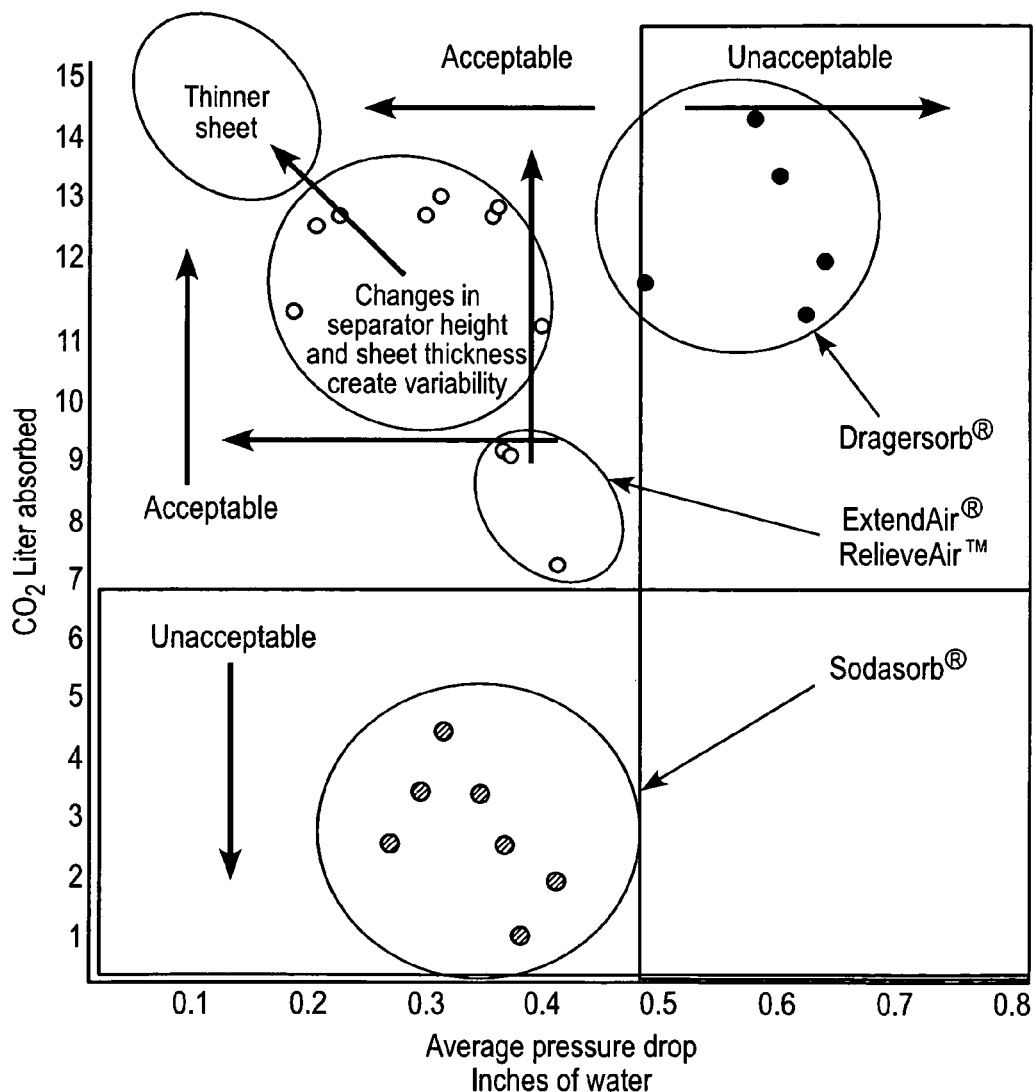
FIG. 10 is a graph of $CO_2$ adsorbed over average pressure drop.

FIG. 10 illustrates total liters of $CO_2$ adsorbed versus an average pressure drop or breathing resistance (inches of water), while lowering inhaled $CO_2$ (1000 ppm) by a minimum of 30%. By further reducing the sheet thickness and varying the separator height an optimum configuration can be achieved.

Figure 11:
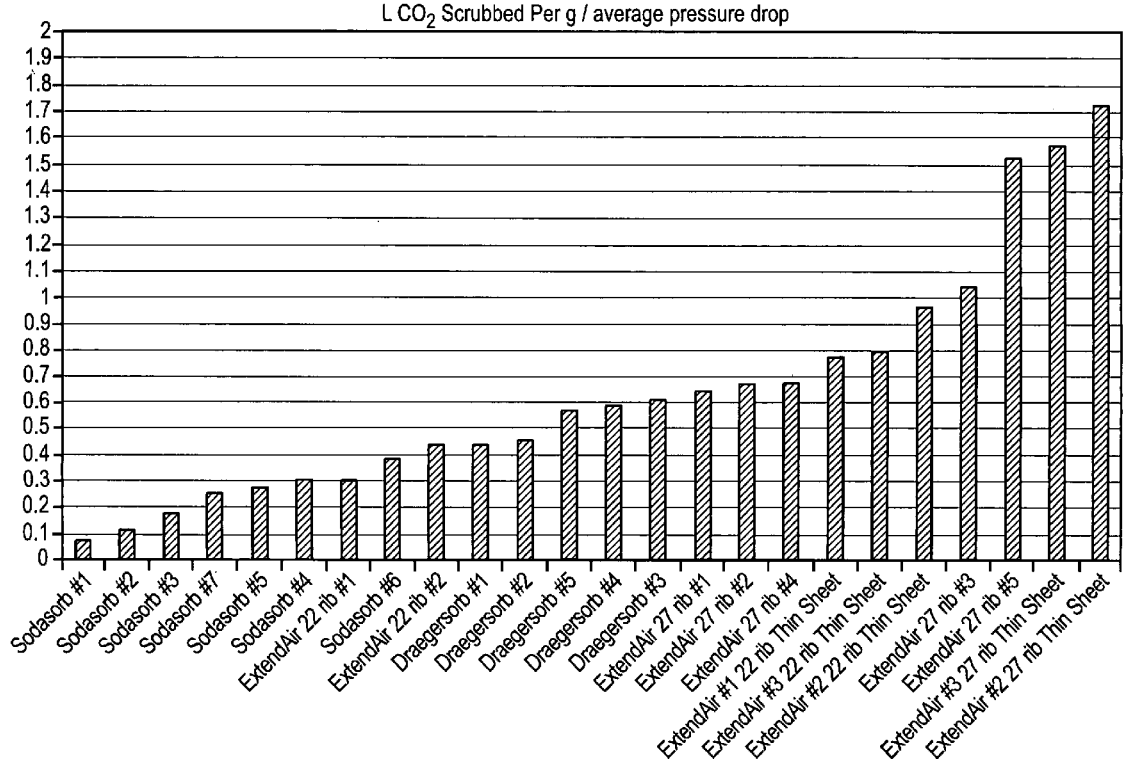
FIG. 11 is a graph of liters of $CO_2$ per gram adsorbed over average pressure drop for different granule adsorbents and various configurations of sheet and rib heights.

FIG. 11 illustrates amount of $CO_2$ adsorbed by weight over average pressure drop. By reducing the sheet thickness a ratio of 2.0 or higher may be expected, while lowering inhaled $CO_2$ (1000 ppm) by a minimum of 30%.

Figure 12:
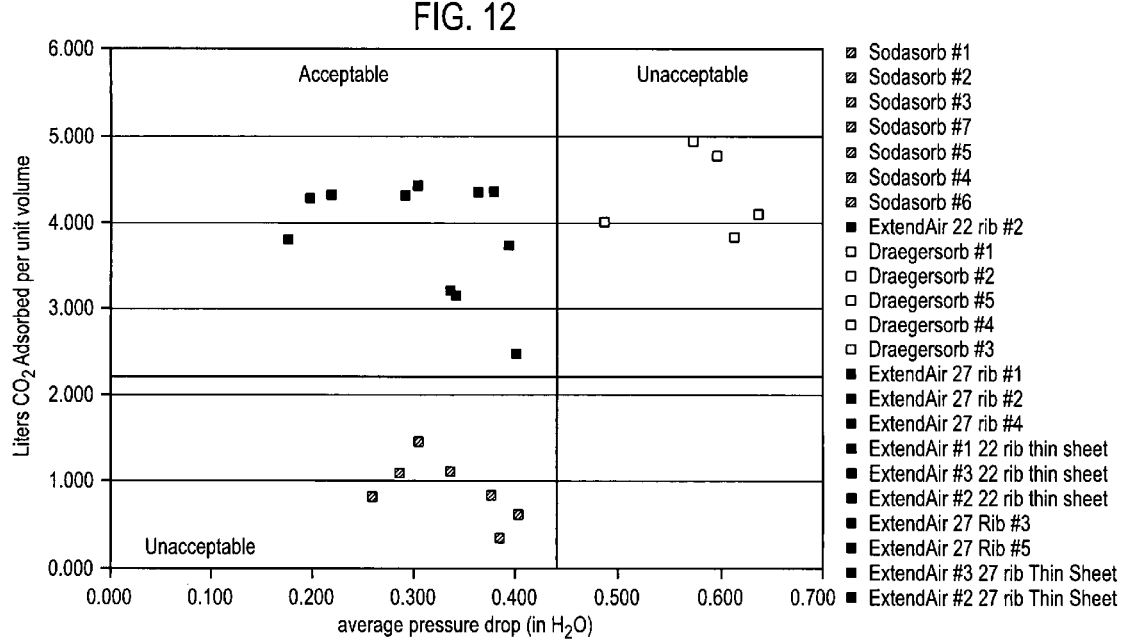
FIG. 12 is a graph of $CO_2$ adsorbed per unit volume over average pressure drop.

FIG. 12 illustrates liters of $CO_2$ adsorbed per unit volume (liters per cubic inch) over average pressure drop (inches of water), while lowering inhaled $CO_2$ (100 ppm) by a minimum of 30%. In certain embodiments, carbon dioxide adsorbed per unit volume is greater than about 2.0 liters per cubic inch and average pressure drop is less than about 0.045 inches of $H_2O$. Reducing the sheet thickness and varying the separator height can produce an optimum configuration.

The present invention may maintain inherent resilience to shock and vibration while being handled by the patient in their normal day-to-day activities and does so without degradation of performance. The present invention may not experience any change in performance or operation, due to inherent structural rigidity, when the orientation changes, e.g., horizontal rather than vertical. This may be a requirement for portability.

Figure 13:
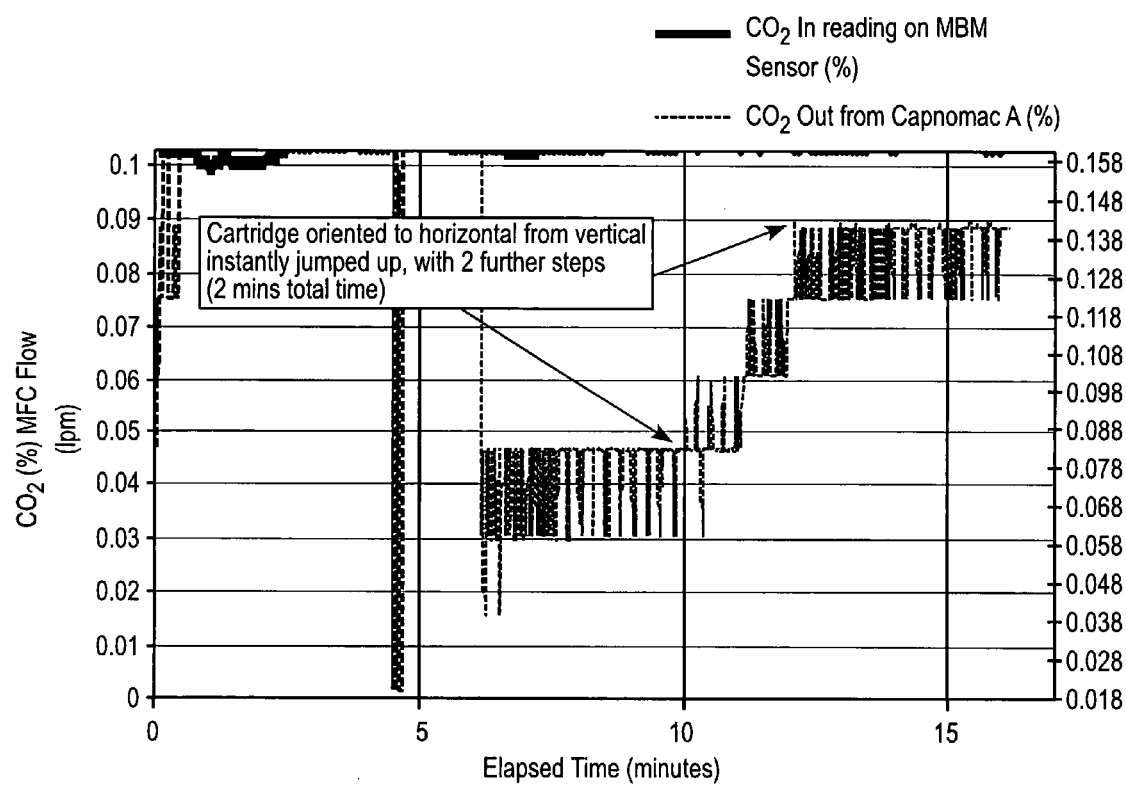
FIG. 13 is a graph of reduced $CO_2$ adsorption when a housing containing granular adsorbents is re-orientated from the vertical to horizontal plane.

As shown in FIG. 13, a significant decrease (45%) in $CO_2$ adsorption was recorded when the housing contained granular based adsorbent was re-orientated from the vertical to horizontal plane. Typical absorptive degradation, when re-orientation performed, ranged from 15% to 45% or more. This effect can somewhat be reduced by the introduction of foam, for example, to keep the granules compressed, but this reduces the space available for adsorbent granules The present invention may reduce inhaled $CO_2$ (1000 ppm by a minimum 300 ppm) over a minimum period of 120 minutes, with a ideal duration of 180 minutes or longer, allowing for use with both a single long anxiety attack or multiple short anxiety attacks.

The present invention may be stored between anxiety attacks by means of a sealing cap to mimmize the passive exhaustion of the adsorbent material. Additionally, the present invention can be stored in a re-sealable bag to further minimize the passive exhaustion of the adsorbent material between anxiety attacks.

The present invention may maintain the inherent capability of the adsorbent sheet in its ability to effectively perform in a range of temperature environments.

Figure 14B:
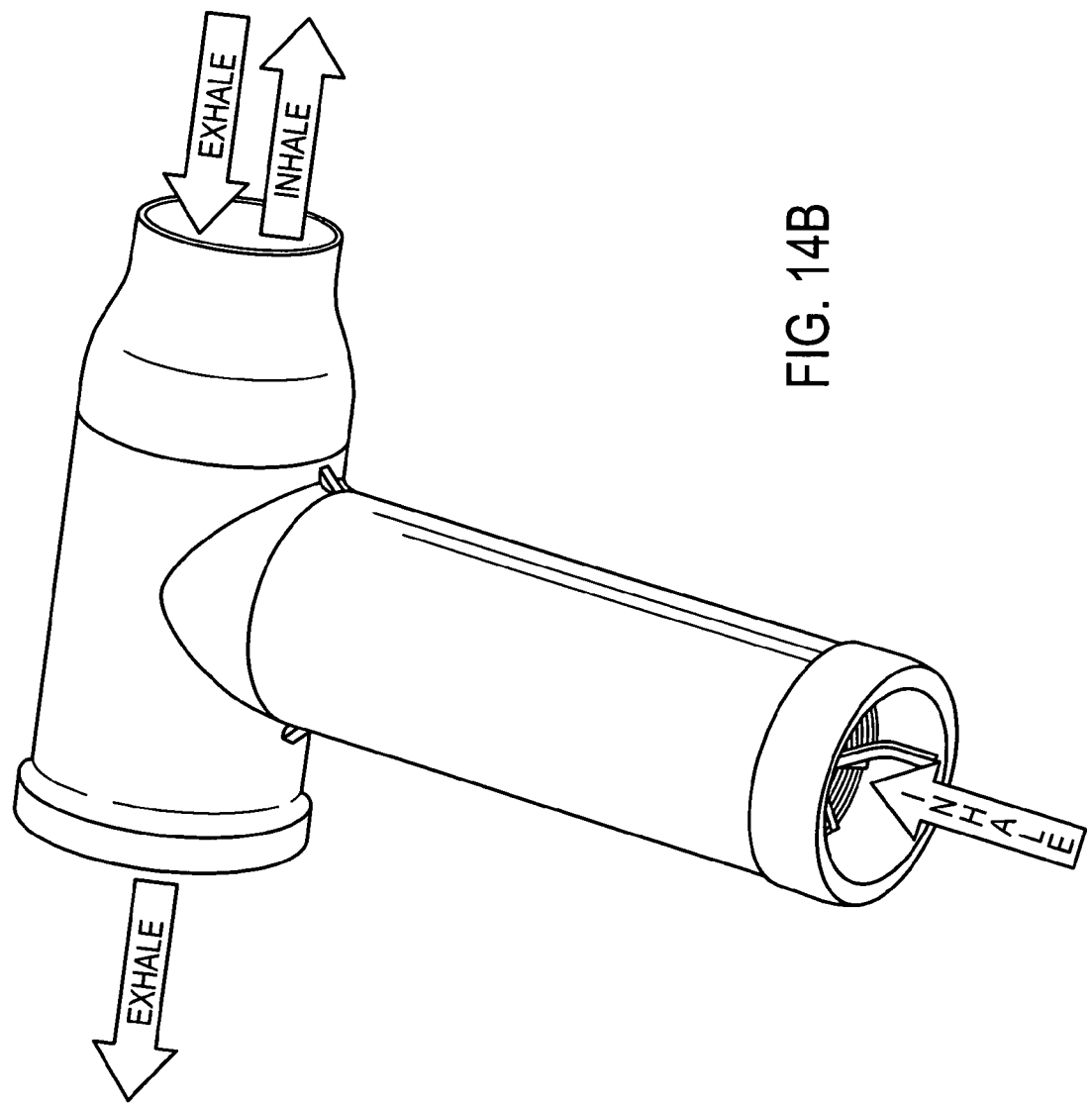

As shown in FIGS. 14a and 14b, embodiments of the present invention may include an inhalation device for treating patients prone to panic attacks using the $CO_2$ adsorbent described herein. FIG. 14a is a perspective view of the inhalation device depicting air flow for air passing through the $CO_2$ adsorbent cartridge of the present invention. As shown, both inhaled air and exhaled breath pass through the system, however the one way valves direct inhaled air through the $CO_2$ adsorbent, and direct exhaled air to be vented directly. In certain other embodiments, inhaled air and exhaled air contacts the adsorbent material within an inhalation device. FIG. 14b is a cross-section view of an inhalation device indicating the location for the $CO_2$ adsorbent cartridge of the present invention, and also the flow directions of the preferred embodiment.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. An adsorbent cartridge suitable for adsorbing gas contaminants from a gas comprising a rolled or stacked extruded, ribbed sheet comprising a polymer and an adsorbent material selected from calcium hydroxide, lithium hydroxide, molecular sieves, and activated carbon, wherein the ribs are integral to the sheet, wherein the ribs create channels for gas flow when the sheet is rolled or stacked without need of an external separator to create the channels, wherein the base sheet thickness is about 0.001 inches to 0.030 inches; and wherein no other supporting fabric or material is needed to maintain structural integrity of the ribbed sheet.

2. The cartridge of claim 1, wherein the base sheet thickness is about 0.010 to 0.030 inches.

3. The cartridge of claim 1, wherein the base sheet thickness is about 0.001 to 0.010 inches.

4. The cartridge of claim 1, wherein the sheet is rolled.

5. The cartridge of claim 1, wherein levels of inhaled $CO_2$ (1000 ppm) are lowered by a minimum of approximately 30% for a period up to approximately 180 minutes or more, while maintaining an average breathing resistance of less than approximately 0.4 inches of water and a maximum of less than approximately 1.332 inches of water.

6. The cartridge of claim 1, wherein levels of inhaled $CO_2$ (1000 ppm) are lowered by a minimum of approximately 50% for a period up to approximately 120 minutes or more, while maintaining an average breathing resistance of less than approximately 0.4 inches of water and a maximum of less than approximately 1.332 inches of water.

7. The cartridge of claim 1, wherein levels of inhaled $CO_2$ (1000 ppm) are lowered by a minimum of approximately 70% for a period up to approximately 45 minutes or more, while maintaining an average breathing resistance of less than approximately 0.32 inches of water and a maximum of less than approximately 1.080 inches of water.

8. An inhalation device comprising:
a housing;
the absorbent cartridge of claim 1 within the housing;
wherein the cartridge is positioned such that airflow through the housing passes across but not through the sheet.

9. The inhalation device of claim 8, wherein the cartridge is replaceable.

10. The inhalation device of claim 8, wherein the sheet is rolled.

11. A personal adsorption device capable of being handheld by a patient during use, the device comprising the adsorbent of claim 1.

12. A method of alleviating symptoms of anxiety attacks, the method comprising:
providing a device comprising:
a housing;
the adsorbent cartridge of claim 1 within the housing;
wherein the cartridge is positioned such that airflow through the housing passes across but not through the sheet.

13. The method of claim 12, wherein the sheet is rolled.

14. The inhalation device of claim 8, wherein the base sheet thickness is about 0.010 to 0.030 inches.

15. The inhalation device of claim 8, wherein the base sheet thickness is about 0.001 to 0.010 inches.

16. The personal adsorption device of claim 11, wherein the base sheet thickness is about 0.010 to 0.030 inches.

17. The personal adsorption device of claim 11, wherein the base sheet thickness is about 0.001 to 0.010 inches.

18. The method of claim 12, wherein the base sheet thickness is about 0.010 to 0.030 inches.

19. The method of claim 12, wherein the base sheet thickness is about 0.001 to 0.010 inches.

20. An adsorbent cartridge suitable for adsorbing gas contaminants from a gas comprising a rolled or stacked extruded, ribbed sheet comprising a polymer and an adsorbent material selected from calcium hydroxide and lithium hydroxide, wherein the ribs are integral to the sheet, wherein the ribs create channels for gas flow when the sheet is rolled or stacked without need of an external separator to create the channels, wherein the base sheet thickness is about 0.010 inches to 0.030 inches; and wherein no other supporting fabric or material is needed to maintain structural integrity of the ribbed sheet.

21. The cartridge of claim 20, wherein the adsorbent material is calcium hydroxide.

* * * * *

UNITED STATES PATENT AND TRADEMARK OFFICE
CERTIFICATE OF CORRECTION

PATENT NO. : 8,413,655 B2  Page 1 of 1
APPLICATION NO. : 12/482286
DATED : April 9, 2013
INVENTOR(S) : Douglas B. McKenna and Nicholas J. Dunlop It is certified that error appears in the above-identified patent and that said Letters Patent is hereby corrected as shown below:

In the Claims

In column 10, line 5 of Claim 8, delete "absorbent" and insert -- adsorbent --, therefor.

Signed and Sealed this
Twenty-third Day of September, 2014

Michelle K. Lee
*Deputy Director of the United States Patent and Trademark Office*